United States Patent
Dent et al.

(10) Patent No.: US 11,573,226 B2
(45) Date of Patent: Feb. 7, 2023

(54) SYSTEMS AND METHODS FOR AFFINITY CAPILLARY ELECTROPHORESIS

(71) Applicant: GENENTECH, INC., South San Francisco, CA (US)

(72) Inventors: Kelsey Catherine Dent, South San Francisco, CA (US); David John Fischer, South San Francisco, CA (US); David A. Michels, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 309 days.

(21) Appl. No.: 16/567,664

(22) Filed: Sep. 11, 2019

(65) Prior Publication Data
US 2020/0081003 A1    Mar. 12, 2020

Related U.S. Application Data

(63) Continuation of application No. PCT/US2019/050361, filed on Sep. 10, 2019.
(Continued)

(51) Int. Cl.
*G01N 33/561* (2006.01)
*B01L 3/00* (2006.01)
*G01N 27/447* (2006.01)

(52) U.S. Cl.
CPC ............ *G01N 33/561* (2013.01); *B01L 3/502* (2013.01); *G01N 27/44747* (2013.01);
(Continued)

(58) Field of Classification Search
CPC .. G01N 33/561; G01N 33/536; G01N 33/563; G01N 33/50; G01N 33/53;
(Continued)

(56) References Cited

U.S. PATENT DOCUMENTS

2003/0078385 A1    4/2003  Arathoon et al.
2003/0207346 A1    11/2003 Arathoon et al.
(Continued)

FOREIGN PATENT DOCUMENTS

WO    WO 2005/016956 A1    2/2005
WO    WO 2007/147901 A1    12/2007
(Continued)

OTHER PUBLICATIONS

Kumari et al., Analytical Biochemistry, 2019, 566, 20-22 (Year: 2019).*
(Continued)

*Primary Examiner* — Gurpreet Kaur
(74) *Attorney, Agent, or Firm* — Baker Botts L.L.P.

(57) ABSTRACT

The presently disclosed subject matter relates to compositions, systems and methods of screening one or more species of polypeptide in a complex mixture of polypeptides, e.g., multi-subunit proteins. For example, the subject matter relates to ligands used in connection with affinity capillary electrophoresis, as well as methods and systems for detecting polypeptides in a mixture of multimers that include multispecific antibodies, e.g., bispecific antibodies.

28 Claims, 16 Drawing Sheets

Related U.S. Application Data

(60) Provisional application No. 62/729,384, filed on Sep. 10, 2018.

(52) U.S. Cl.
CPC .............................. *G01N 27/44791* (2013.01); *B01L 2300/0663* (2013.01); *B01L 2300/0838* (2013.01); *B01L 2400/0406* (2013.01); *B01L 2400/0421* (2013.01)

(58) Field of Classification Search
CPC ........... G01N 33/531; G01N 27/44791; G01N 27/44747; C07K 1/26; B01L 2300/0663; B01L 2300/0838; B01L 2400/0406; B01L 2400/0421; B01L 3/502
See application file for complete search history.

(56) References Cited

U.S. PATENT DOCUMENTS

| | | | |
|---|---|---|---|
| 2013/0171095 A1* | 7/2013 | Bernett | C07K 16/2803 435/328 |
| 2015/0004168 A1* | 1/2015 | Heldwein | A61P 9/10 424/139.1 |
| 2017/0045527 A1* | 2/2017 | Muthusamy | G01N 33/6854 |
| 2019/0270814 A1* | 9/2019 | Ellerman | A61K 9/0019 |

FOREIGN PATENT DOCUMENTS

| | | |
|---|---|---|
| WO | WO 2009/089004 A1 | 7/2009 |
| WO | WO 2015/095392 A1 | 6/2015 |
| WO | WO 2016/183222 A1 | 11/2016 |

OTHER PUBLICATIONS

Chothia et al., "Canonical Structures for the Hypervariable Regions of Immunoglobulins," J. Mol. Biol. 196:901-917 (1987).
Clackson et al., "Making antibody fragments using phage display libraries," Nature 352:624-628 (1991).
Flatman et al., "Process analytics for purification of monoclonal antibodies," J. Chromatogr. B 848:79-87 (2007).
International Search Report dated Dec. 16, 2019 in International Application No. PCT/US2019/050361.
Kabat et al., Sequences of Proteins of Immunological Interest, 5th Ed. Public Health Service, National Institutes of Health, Bethesda, MD, 1991.
Kindt et al., Kuby Immunology, 6th ed., W.H. Freeman and Co., p. 91 (2007).
MacCallum et al., "Antibody-antigen Interactions: Contact Analysis and Binding Site Topography," J. Mol. Biol. 262:732-745 (1996).
Pack et al., "Improved Bivalent Miniantibodies, with Identical Avidity as Whole Antibodies, Produced by High Cell Density Fermentation of *Escherichia coli*," Bio/Technology 11:1271-1277 (1993).
Pack et al., "Miniantibodies: Use of Amphipathic Helices To Produce Functional, Flexibly Linked Dimeric Fv Fragments with High Avidity in *Escherichia coli*," Biochemistry 31(6):1579-1584 (1992).
Portolano et al., "Lack of Promiscuity in Autoantigen-Specific H and L Chain Combinations as Revealed by Human H and L Chain 'Roulette'," J. Immunol. 150(3):880-887(1993).

* cited by examiner

| Peptide | Mass (Da) | pI | Charge (@ pH 5.7) |
|---|---|---|---|
| Peptide | 1751 | 3.75 | -2.9 |
| +E | 1866 | 3.65 | -3.8 |
| +D | 1880 | 3.55 | -3.9 |
| +DD | 1981 | 3.45 | -4.8 |
| +DDD | 2096 | 3.35 | -5.8 |

SYSTEMS AND METHODS FOR AFFINITY CAPILLARY ELECTROPHORESIS

CROSS-REFERENCE TO RELATED APPLICATIONS

This application is a continuation of International Patent Application No. PCT/US19/50361, filed Sep. 10, 2019, which claims priority to U.S. Provisional Patent Application Ser. No. 62/729,384, filed Sep. 10, 2018, the contents of which are incorporated by reference in their entirety.

TECHNICAL FIELD

The presently disclosed subject matter relates to compositions, systems and methods of screening one or more species of polypeptide in a complex mixture of polypeptides. In particular, the subject matter disclosed herein relates to ligands used in connection with affinity capillary electrophoresis, as well as methods and systems for detecting polypeptides in a mixture of multimers that include multispecific antibodies, e.g., bispecific antibodies.

BACKGROUND

Bispecific antibodies (BsAbs) have attracted widespread therapeutic interest in recent years due to their unique ability to recognize two distinct antigen targets. Despite the interest in the therapeutic use of BsAbs, their commercial production has been challenging because conventional production methods can result in undesirable byproducts and require complex purification processes. For example, certain BsAbs have been generated via knob-into-hole technology, whereby complementary mutations are made in the CH3 domain of the heavy chains to form "knob" and "hole" structures. In contrast to the production of conventional antibodies, which can rely on the dimerization of identical heavy-chain/light-chain subunits, when using knob-into-hole technology, large amino acid side chains are introduced into the CH3 domain of one of the heavy chains and those side chains fit into appropriately designed cavities in the CH3 domain of another heavy chain. Chain mispairings (e.g., homo-dimerization of identical heavy chain peptides or improper heavy-chain/light-chain associations) can be observed resulting in a unique set of product-related impurities, including both knob-knob and hole-hole homodimer (HD) species. These homodimer variants can be challenging to quantitate as they can be present at low levels and have physicochemical characteristics that are highly similar to the intended BsAb product and other BsAb molecular variants.

Thus, there remains a need for systems and techniques to purify and quantitate the target BsAb from undesirable protein produces.

SUMMARY OF THE INVENTION

The presently disclosed subject matter relates to compositions, systems and methods of screening one or more species of polypeptide in a complex mixture of polypeptides. In particular, the subject matter disclosed herein relates to ligands used in connection with affinity capillary electrophoresis, as well as methods and systems for detecting polypeptides in a mixture of multimers that include multispecific antibodies, e.g., bispecific antibodies.

In certain embodiments, the present disclosure is directed to systems for separating multi-subunit proteins in a sample comprising: a) a ligand, b) a background electrolyte buffer, c) the sample, d) a capillary, e) an anode at or near one end of the capillary, and f) a cathode at or near the other end of the capillary, wherein the sample is mixed with the ligand to form at least one ligand-protein complex and loaded into the capillary at the anode end of the capillary, and wherein the capillary is filled with the background electrolyte buffer mixed with the ligand.

In certain embodiments the systems of the present disclosure further comprise a detector located near the cathode end of the capillary, wherein the detector detects 210 nm to 220 nm light absorbance or laser induced fluorescence.

In certain embodiments, the systems of the present disclosure comprise a sample where the sample comprises at least one homodimer, at least one heterodimer, or combination thereof. In certain embodiments, the systems of the present disclosure comprise a first ligand-protein complex, which is formed when the ligand binds to the first subunit of the at least one heterodimer and does not bind to the second subunit of the at least one heterodimer. In certain embodiments, the systems of the present disclosure comprise a second ligand-protein complex, which is formed when the ligand binds to the at least two identical first or second subunits of the homodimer. In certain embodiments, the at least one ligand-protein complex is configured to have a fluorescent (or otherwise detectable) label, or an altered charge, mass, hydrodynamic size, electrophoretic mobility, or a combination of thereof when the ligand binds to the subunits of the multi-subunit protein. In certain embodiments, the second ligand-protein complex has a lower electrophoretic mobility than the first ligand-protein complex.

In certain embodiments, the systems of the present disclosure comprise a ligand where the ligand is a polypeptide or a polypeptide fragment. In certain embodiments, the ligand is a fluorescent labeled polypeptide or a fluorescent labeled polypeptide fragment. In certain embodiments, the ligand is selected from the group consisting of a human CD3 polypeptide, a mouse CD3 polypeptide, a rat CD3 polypeptide, a rabbit CD3 polypeptide, and a cynomolgus monkey CD3 polypeptide. In certain embodiments, the ligand is modified by adding one or more amino acids to a non-binding region of the ligand. In certain embodiments, the one or more amino acids are selected from the group consisting of a glutamic acid, an aspartic acid, and a combination thereof. In certain embodiments, the added one or more amino acids is configured to alter a charge and a mass of the ligand.

In certain embodiments, the systems of the present disclosure comprise a sample where the sample is further mixed with the ligand in a low pH urea buffer. In certain embodiments, the present disclosure is directed to methods further comprising mixing a high pH HEPES buffer and 0.1% PS20 to the mixture of the sample and the ligand. In certain embodiments, the systems of the present disclosure comprise a background electrolyte buffer where the background electrolyte buffer comprises Amino-n-Caproic Acid (EACA), a Triethylene tetramine (TETA), and Hydroxypropylmethyl-cellulose (HPMC). In certain embodiments, the background electrolyte buffer comprises the ligand that binds to a first subunit of the at least one heterodimer of the above-described methods and does not bind to the second subunit of the at least one heterodimer.

In certain embodiments, the present disclosure is directed to methods for separating multi-subunit proteins in a sample comprising the steps of: (a) creating a mixture of the sample and a ligand to form at least one ligand-protein complex, (b) applying the mixture to a capillary, wherein the capillary is filled with a background electrolyte buffer mixed with the ligand, (c) applying a voltage across the capillary, and (d) allowing the multi-subunit proteins and at least one ligand-protein complex to move through the capillary, wherein the ligand-protein complex is configured to have a fluorescent (or otherwise detectable) label, an altered charge, mass, hydrodynamic size, electrophoretic mobility, or a combination thereof when the ligand binds to subunits of the multi-subunit protein to thereby separate the multi-subunit proteins in the sample.

In certain embodiments, the present disclosure is directed to methods for isolating a target protein in a sample mixture comprising the steps of: (a) creating a mixture of the sample and a ligand to form at least one ligand-protein complex, (b) applying the mixture to a capillary, wherein the capillary is filled with a background electrolyte buffer mixed with the ligand, (c) applying a voltage across the capillary, (d) allowing the multi-subunit proteins and the at least one ligand-protein complex to move through the capillary, wherein the ligand-protein complex is configured to have a fluorescent (or otherwise detectable) label, an altered charge, mass, hydrodynamic size, electrophoretic mobility, or a combination thereof when the ligand binds to subunits of the multi-subunit protein, and (e) isolating the target protein, which is separated from non-target proteins.

In certain embodiments, the present disclosure is directed to methods employing a capillary, wherein the capillary comprises a cathode end, an anode end, and a detector. In certain embodiments, the capillary has an inner diameter of about 50 μm. In certain embodiments, the capillary has a distance to detector of about 20 cm. In certain embodiments, the capillary has a total lengthy of about 30 cm. In certain embodiments, the detector is near the cathode end of the capillary and detects 210 nm to 220 nm light absorbance or laser induced fluorescence. In certain embodiments, the voltage is 30 kilovolts.

In certain embodiments, the present disclosure is directed to methods where a sample is utilized, wherein the sample comprises at least one homodimer, at least one heterodimer, or combination thereof, wherein the at least one heterodimer comprises a first subunit and a second subunit, and the at least one homodimer comprises at least two identical first or second subunits. In certain embodiments, the at least one heterodimer comprises a bispecific antibody. In certain embodiments, the at least one homodimer comprises a monoclonal antibody.

In certain embodiments, the present disclosure is directed to methods utilizing a ligand, wherein the ligand is a peptide or a peptide fragment. In certain embodiments, the ligand is a fluorescent labeled peptide or a fluorescent labeled peptide fragment. In certain embodiments, the ligand is selected from the group consisting of a human CD3 peptide, a mouse CD3 peptide, a rat CD3 peptide, a rabbit CD3 peptide, and a cynomolgus monkey CD3 peptide. In certain embodiments, the ligand is configured to be modified by adding one or more amino acids to a non-binding region of the ligand. In certain embodiments, the one or more amino acids are selected from the group consisting of a glutamic acid, an aspartic acid, and a combination thereof. In certain embodiments, the added one or more amino acids is configured to alter a charge and a mass of the ligand.

In certain embodiments, the present disclosure is directed to methods wherein a first ligand-protein complex is formed when the ligand binds to the first subunit of the at least one hetero dimer and does not bind to the second subunit of the at least one hetero dimer. In certain embodiments, the present disclosure is directed to methods wherein a second ligand-protein complex is formed when the ligand binds to the at least two identical first or second subunits of the homodimer.

In certain embodiments, the present disclosure is directed to methods further comprising mixing a low pH urea buffer to the mixture of the sample and the ligand. In certain embodiments, the present disclosure is directed to methods further comprising mixing a high pH HEPES buffer and 0.1% PS20 to the mixture of the sample and the ligand. In certain embodiments, the present disclosure is directed to methods wherein the background electrolyte buffer comprises Amino-n-Caproic Acid (EACA), a Triethylene tetramine (TETA), and Hydroxypropylmethylcellulose (HPMC). In certain embodiments, the background electrolyte buffer comprises the ligand that binds to a first subunit of the at least one heterodimer of the above-described methods and does not bind to the second subunit of the at least one heterodimer.

In certain embodiments, the present disclosure is directed to methods further comprising quantifying the amount of the target protein in the sample.

DETAILED DESCRIPTION

Figure 1:
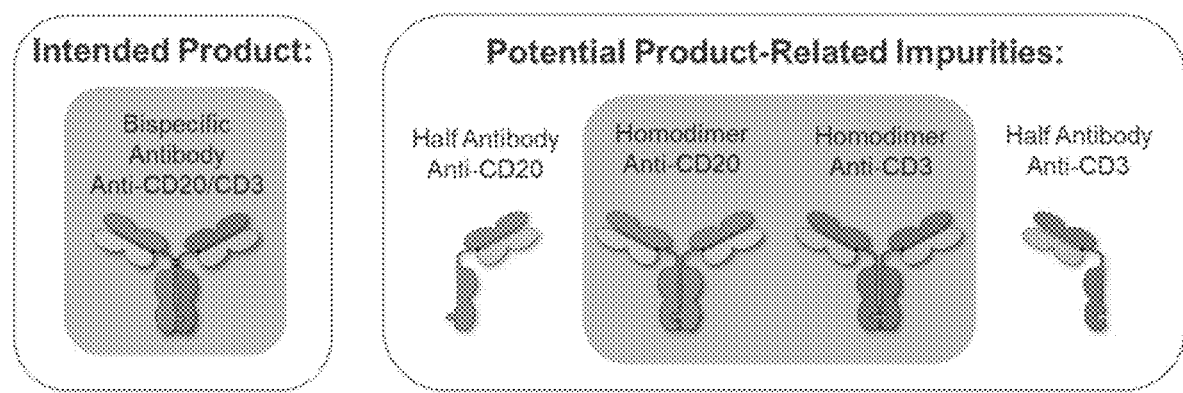
FIG. 1 depicts exemplary bispecific antibodies and product-related impurities (including half antibody and homodimers) having similar physicochemical properties, which make detection challenging by traditional analytical methods.

The subject matter of the present disclosure relates to compositions, systems, and methods for screening one or more species of polypeptide in a complex mixture of polypeptides. For example, but not by way of limitation, the subject matter disclosed herein is applicable to methods of affinity capillary electrophoresis (ACE) to detect target antibodies in a mixture of multimers, including, e.g., multispecific antibodies such as bispecific antibodies. The subject matter of the present disclosure is also directed to ligands and electrophoresis systems used for detecting and isolating such target antibodies. The disclosed electrophoresis methods disclosed herein may be used alone or may be further combined with conventional purification processes and unit operations as are known in the art to achieve particular levels of purity of bispecific antibody, e.g., for therapeutic and/or diagnostic applications.

For purposes of clarity of disclosure and not by way of limitation, the detailed description is divided into the following subsections:
1. Definitions
2. Ligands for Isolating and Quantifying Target Multi-Subunit Proteins
3. System for Isolating and Quantifying Target Multi-Subunit Proteins
4. Methods for Isolating and Quantifying Target Multi-Subunit Proteins

1. Definitions

The practice of the present disclosure will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. As appropriate, procedures involving the use of commercially available kits and reagents are generally carried out in accordance with manufacturer defined protocols and/or parameters unless otherwise noted. Before the present methods, kits and uses therefore are described, it is to be understood that the subject matter of this disclosure is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present disclosure which will be limited only by the appended claims.

As used herein and in the appended claims, the singular forms "a", "and", and "the" include plural referents unless the context clearly dictates otherwise.

The term "about" or "approximately," as used herein, can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" can mean an acceptable error range for the particular value, such as ±10% of the value modified by the term "about."

The term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen) although in certain contexts the interaction can involve a different interaction ratio, e.g., in context of aCD3 homodimer the interaction could be 2:1 because two antigens bind each aCD3 homodimer. The affinity of a molecule X for its partner Y can generally be represented by the dissociation constant ($K_d$). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity; as well as de-immunized, chimeric, humanized and human antibodies and/or antibodies derived from any suitable animal source (e.g., from mice, rats, hamsters, guinea pigs, rabbits, goats, sheep, dogs, horses, cows, monkeys, apes and/or chickens)), immuno-conjugates, synthetic antibodies, single-chain Fvs (scFv), single chain antibodies, Fab fragments, F(ab') fragments, F(ab')2 fragments, disulfide-linked Fvs (sdFv), intrabodies, and epitope-binding fragments of any of the above.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody which binds" an antigen of interest is one that binds the antigen with sufficient affinity such that the antibody is useful as an assay reagent, e.g., as a capture antibody or as a detection antibody. Typically, such an antibody does not significantly cross-react with other polypeptides. With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a target molecule compared to binding of a control molecule, which generally is a molecule of similar structure that does not have binding activity.

The term "anti-CD20 antibody" refers to an antibody that is capable of binding CD20 with sufficient affinity such that the antibody is useful as an agent in targeting CD20, e.g., as an agent in the assays described herein. In certain embodiments, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant ($K_d$) of ≤1 M, ≤100 mM, ≤10 mM, ≤1 mM, ≤100 μM, ≤10 μM, ≤1 μM, ≤100 nM, ≤10 nM, ≤1 nM, ≤0.1 nM, ≤0.01 nM or ≤0.001 nM. In certain embodiments, the $K_d$ of an antibody that binds to CD20, disclosed herein, can be $10^{-3}$ M or less or $10^{-8}$ M or less, e.g., from $10^{-8}$ M to $10^{-13}$ M, e.g., from $10^{-9}$ M to $10^{-13}$ M. In certain embodiments, the $K_d$ of an antibody that binds to CD20, disclosed herein, can be $10^{-10}$ M to $10^{-13}$ M. In certain embodiments, an anti-CD20 antibody binds to an epitope of CD20 that is conserved among CD20 from different species.

The term "anti-CD3 antibody" refers to an antibody that is capable of binding CD3 with sufficient affinity such that the antibody is useful as an agent in targeting CD3, e.g., as an agent in the assays described herein. In certain embodiments, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant ($K_d$) of ≤1 M, ≤100 mM, ≤10 mM, ≤1 mM, ≤100 μM, ≤10 μM, ≤1 μM, ≤100 nM, ≤10 nM, ≤1 nM, ≤0.1 nM, ≤0.01 nM or ≤0.001 nM. In certain embodiments, the $K_d$ of an antibody that binds to CD3, disclosed herein, can be $10^{-3}$ M or less or $10^{-8}$ M or less, e.g., from $10^{-8}$ M to $10^{-13}$ M, e.g., from $10^{-9}$ M to $10^{-13}$ M. In certain embodiments, the $K_d$ of an antibody that binds to CD3, disclosed herein, can be $10^{-10}$ M to $10^{-13}$ M. In certain embodiments, an anti-CD3 antibody binds to an epitope of CD3 that is conserved among CD3 from different species.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

The term "chimeric" antibody refers to an antibody in which a portion of the heavy and/or light chain is derived from a particular source or species, while the remainder of the heavy and/or light chain is derived from a different source or species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

Throughout this specification and claims, the word "comprise," or variations such as "comprises" or "comprising," will be understood to imply the inclusion of a stated integer or group of integers but not the exclusion of any other integer or group of integers.

The terms "correlate" or "correlating" refer to the comparison, in any way, of the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The term "detecting," is used herein, to include both qualitative and quantitative measurements of a target molecule, e.g., CD20 or processed forms thereof. In certain embodiments, detecting includes identifying the mere presence of the target molecule in a sample as well as determining whether the target molecule is present in the sample at detectable levels.

The term "detection means," as used herein, refers to a moiety or technique used to detect the presence of the detectable antibody through signal reporting that is then read out in an assay. Typically, a detection means employ reagents, e.g., a detection agent, that amplify an immobilized label such as the label captured onto a microtiter plate, e.g., avidin, streptavidin-HRP or streptavidin-β-D-galactopyranose.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody" and "whole antibody" are used herein interchangeably to refer to an antibody having a structure substantially similar to a native antibody structure or having heavy chains that contain an Fc region as defined herein.

A "heteromultimer", "heteromultimeric complex", or "heteromultimeric protein" refers to a molecule comprising at least a first hinge-containing polypeptide and a second hinge-containing polypeptide, wherein the second hinge-containing polypeptide differs in amino acid sequence from the first hinge-containing polypeptide by at least one amino acid residue. The heteromultimer can comprise a "heterodimer" formed by the first and second hinge-containing polypeptides or can form higher order tertiary structures where polypeptides in addition to the first and second hinge-containing polypeptides are present. The polypeptides of the heteromultimer may interact with each other by a non-peptidic, covalent bond (e.g., disulfide bond) and/or a non-covalent interaction (e.g., hydrogen bonds, ionic bonds, van der Waals forces, and/or hydrophobic interactions).

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the presently disclosed subject matter. Illustrative examples include but are not limited to, for example, US Patent Application 20030078385 (Arathoon et al.—Genentech; describing knob into holes); WO2007147901 (Kjærgaard et al.—Novo Nordisk: describing ionic interactions); WO 2009089004 (Kannan et al.—Amgen: describing electrostatic steering effects); U.S. Provisional Patent Application 61/243,105 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein.

The terms "host cell," "host cell line," and "host cell culture" as used interchangeably herein, refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), Vols. 1-3. In certain embodiments, for the VL, the subgroup is subgroup kappa I as in Kabat et al., supra. In certain embodiments, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., HVRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein, refers to each of the regions of an antibody variable domain which are hypervariable in sequence (also referred to herein as "complementarity determining regions" or "HVRs") and/or form structurally defined loops ("hypervariable loops") and/or contain the antigen-contacting residues ("antigen contacts"). Unless otherwise indicated, HVR residues and other residues in the variable domain (e.g., FR residues) are numbered herein according to Kabat et al., supra. Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) HVRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

An "immunoconjugate" refers to an antibody conjugated to one or more heterologous molecule(s), including but not limited to a cytotoxic agent.

An "isolated" antibody is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "individual" or "subject," as used interchangeably herein, is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "isolated nucleic acid encoding an antibody" (including references to a specific antibody) refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The terms "multispecific" and "bispecific" mean that the antigen binding molecule is able to specifically bind to at least two distinct antigenic determinants. Typically, a bispecific antigen binding molecule comprises two antigen binding sites, each of which is specific for a different antigenic determinant. In certain embodiments a bispecific antigen binding molecule is capable of simultaneously binding two antigenic determinants, particularly two antigenic determinants expressed on two distinct cells. In one embodiment, the bispecific antibody is a T-cell dependent bispecific (TDB) antibody comprising a first antigen bind site that binds to CD3 and a second antigen bind site that binds to a cell surface antigen. In some embodiments, the cell surface antigen is a tumor antigen, for example, CD20, FcRH5, HER2, CEA, LYPD1, LY6G6D, PMEL17, LY6E, CD19, CD33, CD22, CD79A, CD79B, EDAR, GFRA1, MRP4, RET, Steap1, TenB2, etc. See WO/2015/095392. TDBs engage and activate T cells via the CD3 binding arm and the presence of any anti-CD3 homodimer (CD3 HD) impurity can potentially trigger undesirable off target T-cell activation through bivalent engagement and dimerization of TCR. In certain embodiments, the bispecific antibody comprises less than 2%, 1%, 0.5%, 0.25%, 0.1%, 0.05%, or 0.01% homodimer. In non-limiting embodiments, the bispecific antibody is a TDB antibody, and the homodimer is a CD3 homodimer.

The term "protein," as used herein, refers to any native protein from any vertebrate source, including mammals such as primates (e.g. humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Purified" protein or polypeptide (e.g., antibody), as used herein, refers to a polypeptide that has been increased in purity, such that it exists in a form that is purer than it exists in its natural environment and/or when initially synthesized and/or amplified under laboratory conditions. Purity is a relative term and does not necessarily mean absolute purity.

The term "polypeptide" as used herein, refers to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

A "sample," as used herein, refers to a small portion of a larger quantity of material. In certain embodiments, a sample includes, but is not limited to, cells in culture, cell supernatants, cell lysates, serum, blood plasma, biological fluid (e.g., blood, plasma, serum, stool, urine, lymphatic fluid, ascites, ductal lavage, saliva and cerebrospinal fluid) and tissue samples. The source of the sample may be solid tissue (e.g., from a fresh, frozen, and/or preserved organ, tissue sample, biopsy or aspirate), blood or any blood constituents, bodily fluids (such as, e.g., urine, lymph, cerebral spinal fluid, amniotic fluid, peritoneal fluid or interstitial fluid), or cells from the individual, including circulating cells.

By "mixture" when referring to a mixture of two or more components means that each of the component in the mixture essentially retains its physical and chemical stability in the mixture as evaluated by one or more analytical assays. Exemplary analytical assays for this purpose include: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay. In one embodiment, mixture has been shown to be stable for up to about 8 hours, or up to about 12 hours, or up to about 24 hours at 5° C. or 30° C. In another embodiment, the mixture has been shown to be stable for at least about 8 hours, or at least about 12 hours, or at least about 24 hours at 5° C. or 30° C.

As used herein, the term "subunit" refers to a component of a multimer (e.g., homodimers and heterodimers). The subunit can be a polypeptide which can be any size from three amino acids to several thousands of amino acids long.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In certain embodiments, methods and compositions of the present disclosure are useful in attempts to delay development of a disease or disorder.

An "effective amount" of an agent refers to the amount that is necessary to result in a physiological change in the cell or tissue to which it is administered.

2. Ligands for Isolating and Quantifying Target Multi-Subunit Proteins

The subject matter of the instant disclosure is directed, in certain embodiments, to ligands that can be used in one or more analytical assays. The analytical assays of the present disclosure can, in certain embodiments, separate, isolate, and/or quantify a target protein. Exemplary analytical assays can include: ion-exchange chromatography (IEC), capillary zone electrophoresis (CZE), image capillary isoelectric focusing (iCIEF), and affinity capillary electrophoresis (ACE) assay.

In certain embodiments, the ligands of the present disclosure are capable of binding to (which is used herein to refer to either binding to or being bound by) a target protein. For example, a ligand can bind a target protein when the target protein is in its native conformation, when it is partially unfolded, or totally unfolded. According to the present disclosure, a ligand is not limited to an agent that binds a recognized functional region of the target protein, e.g., the active site of an enzyme, the antigen-combining site of an antibody, the hormone-binding site of a receptor, or a cofactor-binding site. In certain embodiments, the ligand can be an agent that binds to surface or internal sequences as well as conformational domains of the target protein. Furthermore, the ligand may bind to one or more subunits of a target protein (e.g., a first subunit or a second subunit, or both). Therefore, the ligands of the present disclosure encompass agents that in and of themselves may have no apparent biological function, beyond their ability to bind to the target protein in the manner described above.

In certain embodiments the ligand is a polypeptide or polypeptide fragment. In certain embodiments, the ligand comprises an epitope bound by a target protein (e.g., an antibody).

In certain embodiments, the ligand is configured to have a fluorescent (or otherwise detectable) label, an altered charge, mass, hydrodynamic size, electrophoretic mobility, or combination of thereof as compared to the unaltered ligand. In certain embodiments, the ligand is a fluorescent labeled polypeptide or a fluorescent labeled polypeptide fragment. In certain embodiments, the ligand is modified by adding one or more amino acids to a non-binding region of the ligand. In certain embodiments, the one or more amino acids are selected from the group consisting of a glutamic acid, an aspartic acid, and a combination thereof. In certain embodiments, the added one or more amino acids is configured to alter a charge and a mass of the ligand.

In certain embodiments, the ligand is selected from the group consisting of a human CD3 polypeptide, a mouse CD3 polypeptide, a rat CD3 polypeptide, a rabbit CD3 polypeptide, and a cynomolgus monkey CD3 polypeptide. In certain embodiments, the ligand is a CD3 peptide. In certain embodiments, the ligand is a CD3 peptide having the sequence: Pyr DGNEEMGGITQTPYKE acid. In some embodiments, the CD3 peptide can have the sequence: Pyr DGNEEMGGITQTPYKD acid, Pyr DGNEEMGGITQTPYKDD acid, or Pyr DGNEEMGGITQTPYKDDD acid. In non-limiting embodiments, the ligand can include any ligand which can be recognized by a target homodimer.

In certain embodiments, the target protein can include a multi-subunit protein. Subunits can be bound together via any one or more intermolecular bonds (e.g., covalent and non-covalent bonds) to form the multi-subunit protein. In non-limiting embodiments, the multi-subunit protein can be an antibody. Exemplary multi-subunit protein can include monoclonal antibodies, immuno-conjugates, synthetic antibodies, single-chain Fvs (scFv), single chain antibodies, Fab fragments, F(ab') fragments, F(ab')2fragments, disulfide-linked Fvs (sdFv), intrabodies, and epitope-binding fragments of any of the above. In some embodiments, the antibodies can include agonist, antagonist, and neutralizing antibodies, as well as de-immunized, chimeric, humanized and human antibodies and/or antibodies derived from any suitable animal source (e.g., from mice, rats, hamsters, guinea pigs, rabbits, goats, sheep, dogs, horses, cows, monkeys, apes and/or chickens).

In certain embodiments, the multi-subunit protein can be a heterodimer protein. The heterodimer protein can comprise at least a first hinge-containing polypeptide and a second hinge-containing polypeptide, wherein the second hinge-containing polypeptide differs in amino acid sequence from the first hinge-containing polypeptide by at least one amino acid residue. The heterodimer can be formed by the first and second hinge-containing polypeptides or can form higher order tertiary structures where polypeptides in addition to the first and second hinge-containing polypeptides are present. The polypeptides of the heteromultimer can interact with each other by a non-peptide, covalent bond (e.g., disulfide bond) and/or a non-covalent interaction (e.g., hydrogen bonds, ionic bonds, van der Waals forces, and/or hydrophobic interactions). In particular, the heterodimer protein can be bispecific antibodies, which, as understood by one of skill in the art and in certain embodiments, can be comprised of domains from at least two or more different antibodies. In non-limiting embodiments, the bispecific antibody can comprise two different heavy chains (each derived from a different antibody) and two different light chains (each derived from a different antibody), and/or may comprise heavy and light chains each comprising fragments from two or more different antibodies. Furthermore, the bispecific antibody can comprise heavy and/or light chains from de-immunized, murine, chimeric, humanized and human antibodies, as well as combinations heavy and/or light chains from de-immunized, murine, chimeric, humanized, human antibodies and fragments thereof (e.g., variable and/or constant domains thereof). The bispecific antibody of the instant disclosure may also comprise epitope binding fragments of antibodies (for example, but not limited to single-chain Fvs (scFv), single chain antibodies, Fab fragments, F(ab') fragments, F(ab')2fragments, and disulfide-linked Fvs (sdFv)), in particular, linked to one or more heavy or light chain constant domains, e.g., a scFv linked to heavy chain CH1/CH2/CH3 domains. In some embodiments, the bispecific antibody of the present disclosure comprises an Fc domain. As understood by one of skill in the art, the presence of an Fc domain renders the bispecific antibody amenable to purification using Fc-binding moieties. As is well recognized in the art, the particular structure and amino acid sequence of the CH1-hinge-CH2-CH3 domains of the heavy chains determines the immunoglobulin type and subclass. The bispecific antibodies of the present disclosure are not in any manner limited to a specific heavy chain structure or amino acid sequence; accordingly, the bispecific antibodies of the disclosure may be of any type (e.g., IgG, IgE, IgM, IgD, IgA and IgY), class (e.g., IgG1, IgG2, IgG3, IgG4, IgA1 and IgA2) or subclass.

In certain embodiments, the multi-subunit protein can include a homodimer protein. The homodimer protein can have at least two polypeptide chains that are identical or functionally equivalent. For example, a CD20 or a CD3 monoclonal antibody can include two identical heavy chains and light chains. In certain embodiments, the ligand can bind to the multi-subunit protein to form a ligand-protein complex. The ligand can have a specificity for a binding domain of the multi-subunit molecule such as the Fc domain, kappa domain or lambda domain. The ligand-protein complex can have at least one altered property, compared to the multi-subunit protein. In some embodiments, the altered property can include a charge, a mass, a hydrodynamic size, an electrophoretic mobility, and a combination thereof.

3. System for Isolating and Quantifying Target Multi-Subunits Protein

The present disclosure is directed, in certain embodiments, to systems for separating proteins, e.g., multi-subunit proteins, in a sample. In certain embodiments, the systems comprise: a) a ligand, b) a background electrolyte buffer, c) the sample, d) a capillary, e) an anode at or near one end of the capillary, and f) a cathode at or near the other end of the capillary. In certain embodiments, the system will comprise a sample that is mixed with the ligand to form at least one ligand-protein complex. In certain embodiments, the systems comprise such ligand-protein complexes loaded into the capillary at the anode end of the capillary. In certain embodiments, the systems comprise capillaries where the capillary is filled with background electrolyte buffer that has been mixed with the ligand.

In certain embodiments the systems of the present disclosure further comprise a detector located near the cathode end of the capillary. For example, but not by way of limitation, the detector will detect 210 nm to 280 nm light absorbance or laser induced fluorescence. In non-limiting embodiments, the detector can include a fluorescence detector and/or a chemiluminescence detector. A fluorescence detector can detect a ligand tagged with a fluorescence tag. A fluorescence detector can detect an antibody tagged with a fluorescence tag.

As noted above, the systems of the present disclosure also comprise a sample (or are configured to receive a sample). In certain embodiments, the sample comprises at least one homodimer, at least one heterodimer, or combination thereof. In certain embodiments, the systems of the present disclosure comprise a first ligand-protein complex formed when the ligand binds to the first subunit of the at least one heterodimer and does not bind to the second subunit of the at least one heterodimer. In certain embodiments, the systems of the present disclosure comprise a second ligand-protein complex formed when the ligand binds to the at least two identical first or second subunits of a homodimer. In certain embodiments, the at least one ligand-protein complex is configured to have an altered charge, a mass, a hydrodynamic size, an electrophoretic mobility, or a combination of thereof when the ligand binds to the subunits of the multi-subunit protein. In certain embodiments, the second ligand-protein complex can have a lower electrophoretic mobility than the first ligand-protein complex, or vice versa.

In certain embodiments, the systems of the present disclosure comprise a background electrolyte buffer where the background electrolyte buffer comprises Amino-n-Caproic Acid (EACA), a Triethylene tetramine (TETA), and Hydroxypropylmethyl-cellulose (HPMC). In non-limiting embodiments, the systems of the present disclosure comprise a capillary electrophoresis buffer. For example, the capillary electrophoresis buffer comprises phosphate, formate, citrate, acetate, piperazine-N,N'-bis(2-ethanesulfonic acid) (PIPES), phosphate, tricine, phytic, borate/boric acid, Tris, 2-(N-morpholino)ethanesulfonic acid (IVIES), 4-(2-hydroxyethyl)-1-piperazineethanesulfonic acid (HEPES), 3-(N-morpholino)propanesulfonic acid (MOPS), N-cyclohexyl-3-aminopropanesulfonic acid (CAPS), glycine, and bicine. See Handbook of capillary and microchip electrophoresis and associated microtechniques, 3rd addition, Table 1.3 "commonly used CE buffers and their associated properties", page 25. In some embodiments, the systems of the present disclosure comprise capillary electrophoresis additives. For example, the capillary electrophoresis additives include methyl cellulose, sodium dodecyl sulfate (SDS), Polyethylene Glycol (PEG)/Polyethylene oxide (PEO), and/or acetonitrile. In certain embodiments, the systems of the present disclosure comprise a composition including a bispecific antibody which comprises less than 5%, 4%, 3%, 2%, 1%, 0.5%, 0.25%, 0.1%, 0.05%, or 0.01% homodimer. In non-limiting embodiments, the bispecific antibody is a T-cell dependent bispecific (TDB) antibody, and the homodimer is a CD3 homodimer. In some embodiments, the TDB antibody comprises a first antigen bind site that binds to CD3 and a second antigen bind site that binds to a cell surface antigen. TDBs engage and activate T cells via the CD3 binding arm and the presence of any anti-CD3 homodimer (CD3 HD) impurity can potentially trigger undesirable off target T-cell activation through bivalent engagement and dimerization of TCR.

4. Methods for Isolating and Quantifying Target Multi-Subunit Proteins

The present disclosure is directed, in certain embodiments, to methods for separating proteins, e.g., multi-subunit proteins, in a sample. In certain embodiments, the methods comprise the steps of: (a) creating a mixture of the sample comprising at least one protein and a ligand to form at least one ligand-protein complex, (b) applying the mixture to a capillary, wherein the capillary is filled with a background electrolyte buffer mixed with the ligand, (c) applying a voltage across the capillary, and (d) allowing the protein (e.g., a multi-subunit protein) and the at least one ligand-protein complex to move through the capillary. In certain embodiments, the ligand-protein complex is configured to have an altered charge, mass, hydrodynamic size, electrophoretic mobility, or a combination thereof upon ligand binding. In certain embodiments, such alteration facilitates the separation of the proteins in the sample.

The present disclosure is directed, in certain embodiments, to methods for isolating a target protein in a sample mixture comprising the steps of: (a) creating a mixture of a sample comprising a protein and a ligand to form at least one ligand-protein complex, (b) applying the mixture to a capillary, wherein the capillary is filled with a background electrolyte buffer mixed with the ligand, (c) applying a voltage across the capillary, (d) allowing the proteins and the at least one ligand-protein complex to move through the capillary. In certain embodiments, the ligand-protein complex is configured to have an altered charge, mass, hydrodynamic size, electrophoretic mobility, or a combination thereof upon ligand binding to the protein. In certain embodiments, the method further comprises isolating the target protein, which has been separated from non-target proteins present in the sample.

In certain embodiments, the methods of the present disclosure employ a capillary, wherein the capillary comprises a cathode end, an anode end, and a detector. In certain embodiments, the detector is near the cathode end of the capillary and detects 210 nm to 280 nm light absorbance or laser induced fluorescence. In certain embodiments, the voltage can be up to 30 kilovolts. In non-limiting embodiments, length of the capillary can increase to improve separation of the target molecule in a sample.

In certain embodiments, the present disclosure is directed to methods where the sample to be analyzed comprises at least one homodimer, at least one heterodimer, or combination thereof. In certain embodiments, the at least one heterodimer comprises a first subunit and a distinct second subunit. In certain embodiments, the at least one homodimer comprises at least two identical first or second subunits. In certain embodiments, the at least one heterodimer is a bispecific antibody. In certain embodiments, the at least one homodimer is a monoclonal antibody.

In certain embodiments, the present disclosure is directed to methods wherein a first ligand-protein complex is formed where a ligand binds to a first subunit of the at least one heterodimer of the above-described methods and the ligand does not bind to the second subunit of the at least one heterodimer. In certain embodiments, the present disclosure is directed to methods wherein a second ligand-protein complex is formed when the above-described ligand binds to the at least two identical first or second subunits of a homodimer.

In certain embodiments, the present disclosure is directed to methods wherein the background electrolyte buffer comprises Amino-n-Caproic Acid (EACA), a Triethylene tetramine (TETA), and Hydroxypropylmethylcellulose (HPMC). In certain embodiments, the background electrolyte buffer comprises the ligand that binds to a first subunit of the at least one heterodimer of the above-described methods and does not bind to the second subunit of the at least one heterodimer.

In certain embodiments, the methods of the present disclosure can comprise the use of particular buffers and/or other steps to minimize undesirable protein oligomerization. For example, but not by way of limitation, certain proteins present in the sample undergoing analysis, e.g., the anti-CD3 and anti-CD20 homodimer species described in the example below, can form high molecular weight oligomer species. In certain embodiments, such oligomer species can co-migrate with the protein of interest or otherwise impede the utility of the assay. In certain embodiments, e.g., when it is desirable to measure all homodimer in a solution, such oligomer species can be dissociated prior to separation. This can be accomplished, in certain embodiments, by preparing samples in a low pH buffer or a high pH buffer. In non-limiting embodiments, urea can be added into a solution to dissociate the high molecular weight oligomer species prior to separation. In some embodiments, concentration of the solution (e.g., background buffer, capillary electrophoresis buffer, and/or capillary electrophoresis additives) can increase to minimize undesirable protein oligomerization. These conditions have been shown to be sufficient to dissociate the oligomer, yet mild enough to maintain ligand-protein complex formation, without denaturing protein, e.g., BsAb, structure.

In certain embodiments, the methods of the present disclosure can comprise the use of particular buffers and/or other steps to minimize undesirable charged variants of protein of interest. For example, but not by way of limitation, certain proteins present in the sample undergoing analysis, e.g., the anti-CD3 HD described in the Example below, can exhibit charge variation. In certain embodiments, such charge variation is pH dependent. In certain embodiments the use of certain buffers can induce conformation variations that result in observable differences in hydrodynamic size. Accordingly, in certain embodiments, it is desirable to preparing samples in a buffer that will minimize such charge variation or conformational variation. For example, but not by way of limitation, a pH 3.5 buffer can, in certain embodiments, be employed to drive the protein species to a single, low-pH state. In certain embodiments, this is desirable as it can improve the signal to noise ratio, thus lowering the limit of quantitation of the assay. In certain embodiments, however, a pH 7.5 HEPES buffer, e.g., a 10 mM HEPEs buffer at pH 7.5 in conjunction with 0.1% PS20, can be employed to drive the protein species to a single state. In certain embodiments, this is desirable as it can improve the signal to noise ratio, thus lowering the limit of quantitation of the assay.

In certain embodiments, the methods of the present disclosure can comprise the use of particular buffers and/or other steps to minimize protein-surface absorption. For example, but not by way of limitation, certain proteins present in the sample undergoing analysis, e.g., the anti-CD3 HD described in the Example below, can exhibit undesirable surface absorption. Such surface absorption, e.g., to vial walls, can result in lower recoveries of the anti-CD3 homodimer peak area. To control such adsorption and improve recovery, the methods of the present disclosure can include a detergent, e.g., about 0.1% to about 0.4% Polysorbate 20 (PS20), in the sample. In certain embodiments, the methods of the present disclosure can include surfactants where the surfactants can comprise tween 80, poloxamer 188 (p188), triton, SDS, Brij, PEO/PEG and/or glycerol. In non-limiting embodiments, the methods of the present disclosure can include chaotropes such as sucrose, guanidine HCl, and/or cyclodextrins (e.g., various iso-types).

In certain embodiments, the present disclosure is directed to methods further comprising quantifying the amount of the target protein in the sample In addition to the various embodiments depicted and claimed, the disclosed subject matter is also directed to other embodiments having other combinations of the features disclosed and claimed herein. As such, the features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

Embodiments of the Disclosure

The following are non-limiting embodiments of the present disclosure.
1. A system for separating multi-subunit proteins in a sample comprising: a) a ligand, b) a background electrolyte buffer, c) the sample, d) a capillary, e) an anode at or near one end of the capillary, and f) a cathode at or near the other end of the capillary, wherein the sample is mixed with the ligand to form at least one ligand-protein complex and loaded into the capillary at the anode end of the capillary, and wherein the capillary is filled with the background electrolyte buffer mixed with the ligand.
2. The system of embodiment 1, further comprising a detector located near the cathode end of the capillary, wherein the detector detects 210 nm to 220 nm light absorbance or laser induced fluorescence.
3. The system of any one of embodiments 1-2, wherein the sample comprises at least one homodimer, at least one heterodimer, or combination thereof
4. The system of any one of embodiments 1-3, wherein a first ligand-protein complex is formed when the ligand binds to the first subunit of the at least one heterodimer and does not bind to the second subunit of the at least one heterodimer.
5. The system of any one of embodiments 1-4, wherein a second ligand-protein complex is formed when the ligand binds to the at least two identical first or second subunits of the homodimer.
6. The system of any one of embodiments 1-5, wherein the at least one ligand-protein complex is configured to have an altered charge, a mass, a hydrodynamic size, an electrophoretic mobility, or a combination of thereof when the ligand binds to the subunits of the multi-subunit protein.
7. The system of any one of embodiments 1-6, wherein the second ligand-protein complex has a lower electrophoretic mobility than the first ligand-protein complex.
8. The system of any one of embodiments 1-7, wherein the ligand is a peptide or a peptide fragment.
9. The system of any one of embodiments 1-8, wherein the ligand is a fluorescent labeled peptide or a fluorescent labeled peptide fragment.
10. The system of any one of embodiments 1-9, wherein the ligand is selected from the group consisting of a human CD3 peptide, a mouse CD3 peptide, a rat CD3 peptide, a rabbit CD3 peptide, and a cynomolgus monkey CD3 peptide.
11. The system of any one of embodiments 1-10, wherein the ligand is modified by adding one or more amino acids to a non-binding region of the ligand.
12. The system of embodiment 11, wherein the one or more amino acids are selected from the group consisting of a glutamic acid, an aspartic acid, and a combination thereof.
13. The system of any one of embodiments 11-12, wherein the added one or more amino acids is configured to alter a charge and a mass of the ligand.
14. The system of any one of embodiments 11-13, wherein the sample is further mixed with the ligand in: (A) a low pH urea buffer; or (B) a high pH HEPES buffer in combination with 0.1% Polysorbate 20.
15. The system of any one of embodiments 11-14, wherein the background electrolyte buffer comprises Amino-n-Caproic Acid (EACA), a Triethylene tetramine (TETA), and Hydroxypropylmethyl-cellulose (HPMC).
16. A method for separating multi-subunit proteins in a sample comprising the steps of: (a) creating a mixture of the sample and a ligand to form at least one ligand-protein complex, (b) applying the mixture to a capillary, wherein the capillary is filled with a background electrolyte buffer mixed with the ligand, (c) applying a voltage across the capillary, and (d) allowing the multi-subunit proteins and the at least one ligand-protein complex to move through the capillary, wherein the ligand-protein complex is configured to have an altered charge, a mass, a hydrodynamic size, an electrophoretic mobility, or a combination thereof when the ligand binds to subunits of the multi-subunit protein to thereby separate the multi-subunit proteins in the sample.
17. A method for isolating a target protein in a sample mixture comprising the steps of: (a) creating a mixture of the sample and a ligand to form at least one ligand-protein complex, (b) applying the mixture to a capillary, wherein the capillary is filled with a background electrolyte buffer mixed with the ligand, (c) applying a voltage across the capillary, (d) allowing the multi-subunit proteins and the at least one ligand-protein complex to move through the capillary, wherein the ligand-protein complex is configured to have an altered charge, a mass, a hydrodynamic size, an electrophoretic mobility, or a combination thereof when the ligand binds to subunits of the multi-subunit protein, and (e) isolating the target protein, which is separated from non-target proteins.
18. The method of embodiments 16 or claim 17, wherein the capillary comprises a cathode end, an anode end, and a detector.
19. The method of embodiment 18, wherein the detector is near the cathode end of the capillary and detects 210 nm to 220 nm light absorbance or laser induced fluorescence.
20. The method of any one of embodiments 16-19, wherein the voltage is 30 kilovolts.
21. The method of any one of embodiments 16-20, wherein the sample comprises at least one homodimer, at least one heterodimer, or combination thereof, wherein the at least one heterodimer comprises a first subunit and a second subunit, and the at least one homodimer comprises at least two identical first or second subunits.
22. The method of embodiment 21, wherein the at least one heterodimer comprises a bispecific antibody.
23. The method of embodiment 21, wherein the at least one homodimer comprises a monoclonal antibody.
24. The method of any one of embodiments 16-23, wherein the ligand is a peptide or a peptide fragment.
25. The method of any one of embodiments 16-24, wherein the ligand is a fluorescent labeled peptide or a fluorescent labeled peptide fragment.
26. The method of any one of embodiments 16-24, wherein the ligand is selected from the group consisting of a human CD3 peptide, a mouse CD3 peptide, a rat CD3 peptide, a rabbit CD3 peptide, and a cynomolgus monkey CD3 peptide.
27. The method of any one of embodiments 16-24, the ligand is configured to be modified by adding one or more amino acids to a non-binding region of the ligand.

28. The method of embodiment 27, wherein the one or more amino acids are selected from the group consisting of a glutamic acid, an aspartic acid, and a combination thereof.

29. The method of any one of embodiments 27-28, wherein the added one or more amino acids is configured to alter a charge and a mass of the ligand.

30. The method of any one of embodiments 16-29, wherein a first ligand-protein complex is formed when the ligand binds to the first subunit of the at least one hetero dimer and does not bind to the second subunit of the at least one hetero dimer.

31. The method of any one of embodiments 16-30, wherein a second ligand-protein complex is formed when the ligand binds to the at least two identical first or second subunits of the homodimer.

32. The method of any one of embodiments 16-31, further comprising: (A) mixing a low pH urea buffer to the mixture of the sample and the ligand; or (B) mixing a high pH HEPES buffer in combination with 0.1% Polysorbate 20 to the mixture of the sample and the ligand.

33. The method of any one of embodiments 16-32, wherein the background electrolyte buffer comprises Amino-n-Caproic Acid (EACA), a Triethylene tetramine (TETA), and Hydroxypropylmethyl cellulose (HPMC).

34. The method of any one of embodiments 16-33, further comprising quantifying the amount of the target protein in the sample.

35. An affinity capillary electrophoresis ligand comprising a binding region, wherein said binding region binds or is bound by a protein of interest and a modification where said modification facilitates the isolation of the protein of interest.

36. The ligand of embodiment 35 wherein the protein of interest is a homodimer.

37. The ligand of embodiment 35 wherein the protein of interest is a heterodimer.

38. The ligand of embodiment 35 wherein the binding region is a polypeptide.

39. The ligand of embodiment 35 wherein the binding region is a small molecule.

40. The ligand of embodiment 35 wherein the modification is the addition of a fluorescent label or the addition of one or more amino acids to the ligand.

41. The ligand of embodiment 35 wherein the modification provides for a fluorescent label, an altered charge, mass, hydrodynamic size, electrophoretic mobility, or a combination of thereof when the ligand binds to the target protein.

EXAMPLES

The following example is merely illustrative of the presently disclosed subject matter and should not be considered as limiting in any way.

Example 1: Highly Specific Affinity Capillary Electrophoresis (ACE) Method for Detection of Homodimers in Bispecific Products In this example, the specificity and affinity of the BsAb target to the antigen were exploited to achieve a separation based on differences in electrophoretic mobility using capillary zone electrophoresis (CZE).

Materials and Methods

Protein samples were prepared such that the final sample contains either 3 g/L of protein, 50 mM formate, 2M urea, 0.1% PS20, and 50 µM CD3 peptide, pH 3.5 ("Low pH Prep"), or 3 g/L of protein, 10 mM HEPES, 0.1% PS20, and 50 µM CD3 peptide, pH 7.5 (High pH Prep").

Proteins were separated by CZE using a Sciex PA800 Plus instrument equipped with a UV detector and 214 nm filter. The separation was performed using a capillary cartridge with 20/30 cm cartridge (capillary length to detector/total length). The capillary itself was a bare-fused silica capillary with a 50 µm internal diameter.

Samples were separated according to conventional CZE process strategies, except as outlined herein. In brief, samples are injected using a pressure injection for 20 seconds at 0.5 psi. Samples are separated by applying a voltage of 30 kV for 30 minutes. The background electrolyte contains 400 mM Amino-n-Caproic Acid (EACA) buffer with 2 mM Triethylene tetramine (TETA), 0.5% Hydroxypropylmethylcellulose (HPMC), and 50 µM CD3 peptide, at pH 5.7.

Results

Figure 2:
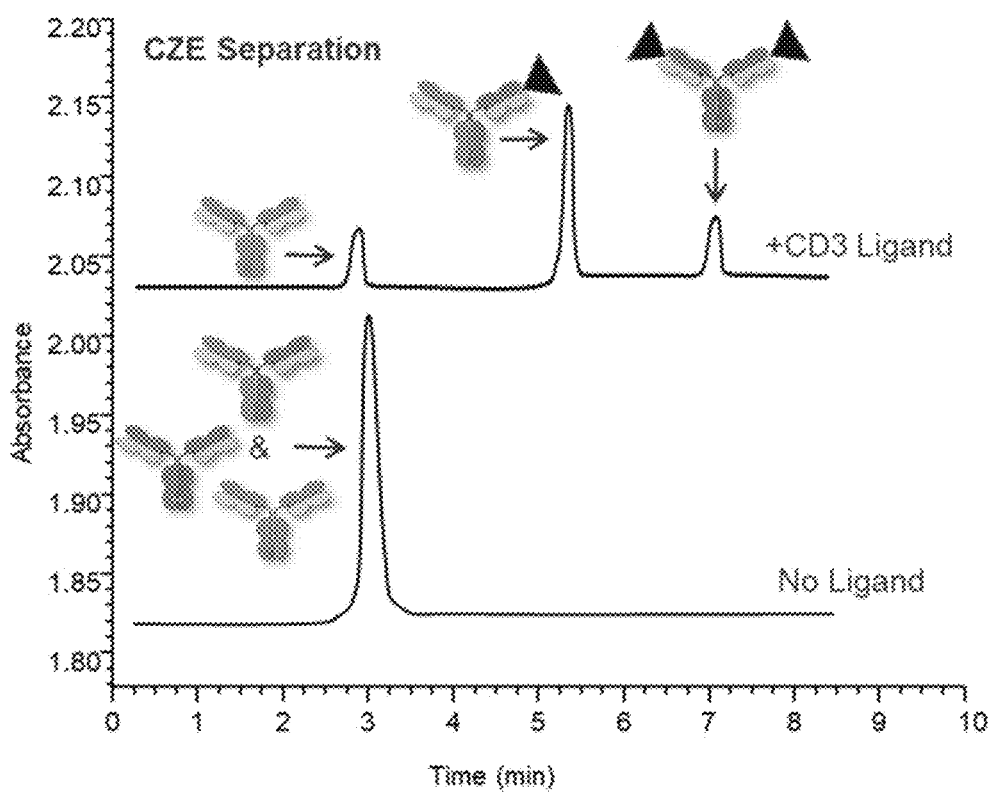
FIG. 2 depicts theoretical separation mechanism of a specific antibody sample by affinity capillary electrophoresis.
Figure 3:
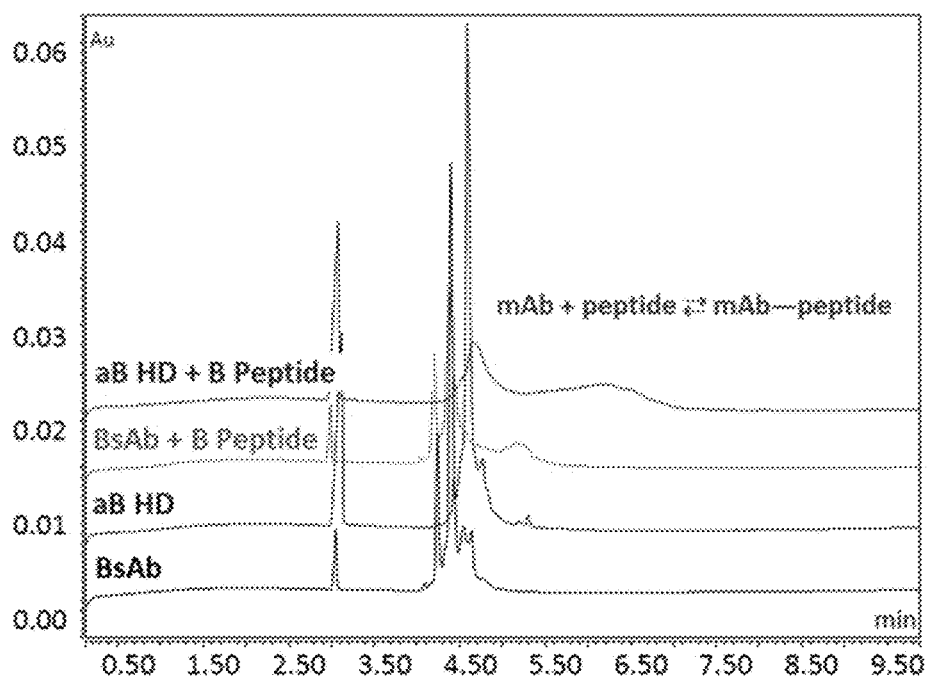
FIG. 3 depicts exemplary affinity capillary electrophoresis for homodimer detection. Incomplete and intermittent complex formation observed when the ligand is mixed with sample prior to separation.

Performance of CZE Method: In classic capillary zone electrophoresis, species migrate and separate based on velocity differences under the influence of an applied electric field. Because the homodimer and bispecific species (FIG. 1) are highly similar in both charge and hydrodynamic size properties, separation of these species by these CZE methods may be insufficient (FIGS. 2 and 3).

ACE with the CD3 Peptide: Applying the principles of affinity CZE, a CD3 peptide was added to the sample mixture to achieve additional separation between these species (FIG. 2). When the peptide was mixed with the sample prior to separation, the migration time of the CD3 binding species shifted due to the apparent change in either charge or hydrodynamic size, or a combination of both. However, the resulting separation profile shows poor peak shape that is consistent with incomplete binding. This may also be due a higher dissociation constant for the anti-CD3-CD3 peptide complex.

Figure 4:
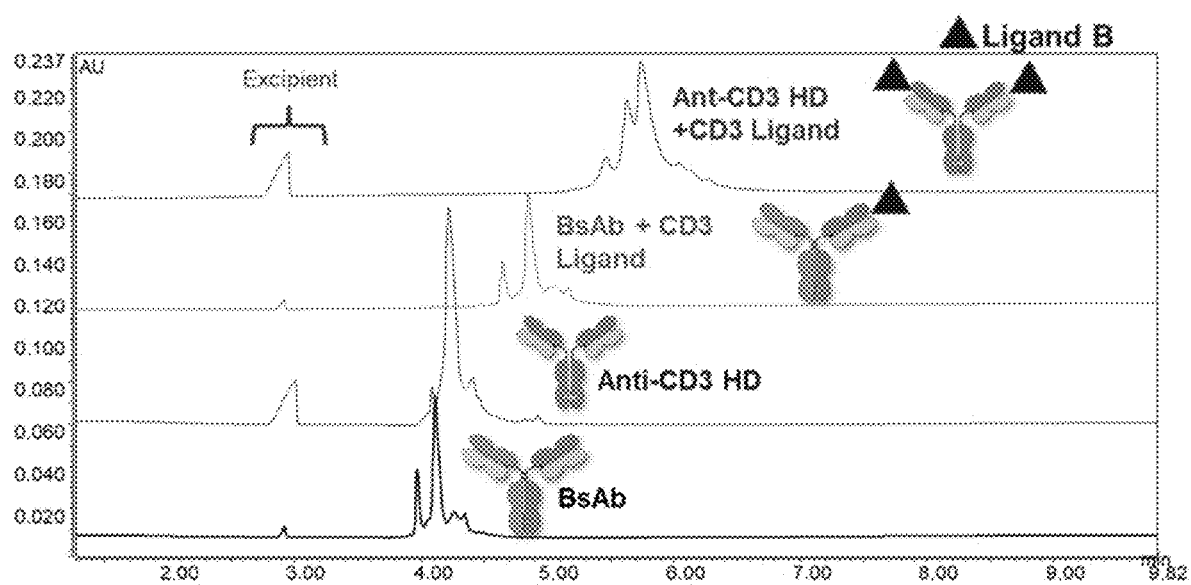
FIG. 4 depicts exemplary performance of affinity electrophoresis with excess ligand added to the background electrolyte.

To improve peak shape and drive towards complete and sustained binding of the CD3 peptide, the peptide was included in both the sample as well as in the background electrolyte at a 50 µM concentration (FIG. 4).

Modifying the CD3 Peptide: As shown in FIG. 4, use of the CD3 peptide resulted in separation between the anti-CD3 HD and the bispecific antibody. These species, however, were not fully (or baseline) resolved. Because low-level, accurate quantitation of the anti-CD3 homodimer was desired, further resolution between the two species was pursued. To achieve this, the CD3 peptide was modified by the addition of various low-isoelectric point (pI) amino acids (e.g. glutamic acid and aspartic acid) to the non-binding N-terminus of the peptide. This process effectively adds charge and mass to the peptide, and ultimately, changes the charge and mass to the bound peptide-antibody complex.

Figures 5A, 5B:
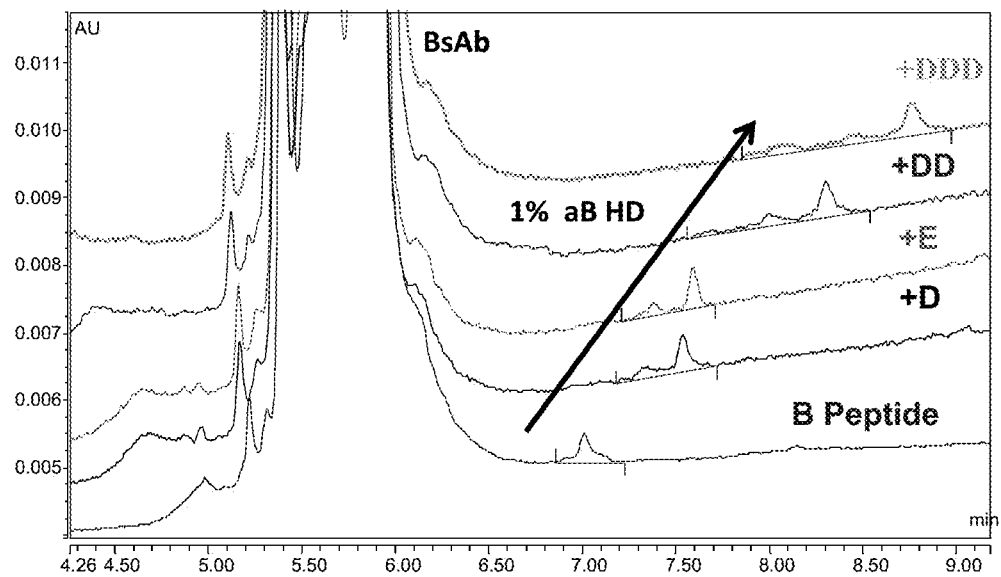
FIG. 5A depicts exemplary modified ligands to improve performance of affinity electrophoresis.
FIG. 5B depicts exemplary performance of affinity electrophoresis with the modified ligands.
Figure 6:
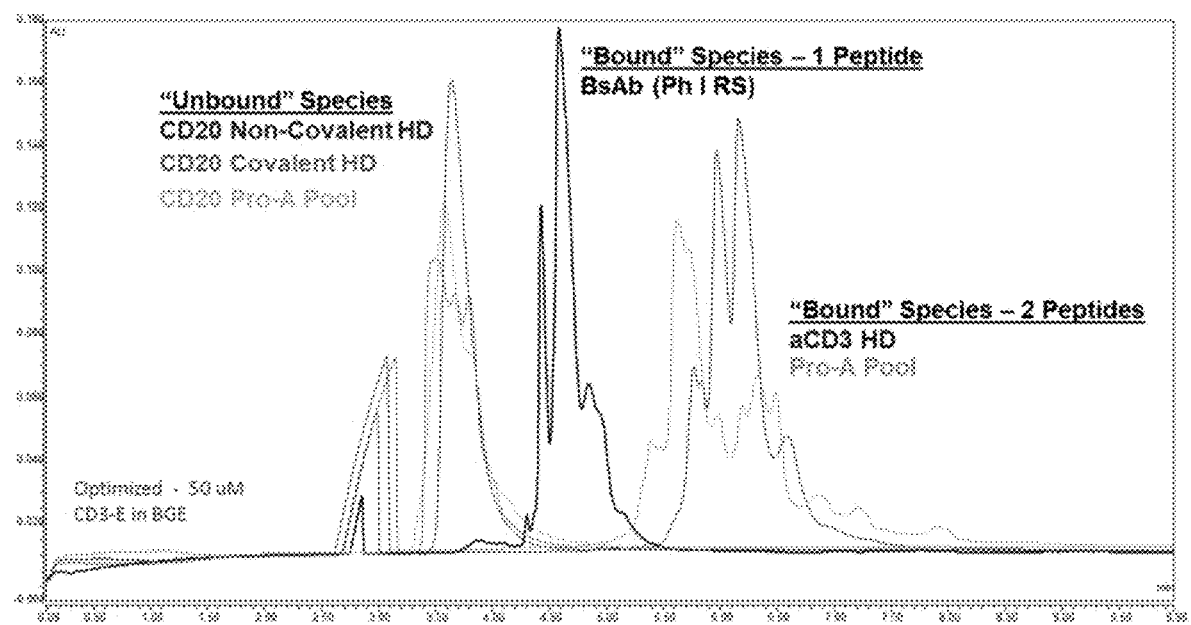
FIG. 6 depicts exemplary performance of the CD3+E Peptide

The CD3 peptide was modified using several amino acid tags, including the addition of one glutamic acid as well as of one, two, and three aspartic acids (FIG. 5A). These peptides were then used in the ACE separation which is shown in FIG. 5B. The larger the charge and mass contribution of the CD3 peptide, the greater the resolution between the species. These modified CD3 peptides, however, also provided greater separation within charged variants of homodimer and bispecific species. This increased resolution within the different charged variants of the homodimer decreases the overall signal to noise ratio of the homodimer peaks, making integration of this region more challenging and ultimately decreasing the sensitivity and limit of quantitation of the assay. As such, modifications to the peptide provided balance between achieving sufficient resolution to minimize interference of bispecific and maximizing the signal of the anti-CD3 homodimer species. For example, and not limitation, the one glutamic acid tag (i.e., CD3-E) provided adequate separation between anti-CD20 and anti-CD3 species, without compromising sensitivity, and as such was selected for this assay (FIG. 6).

Figure 9:
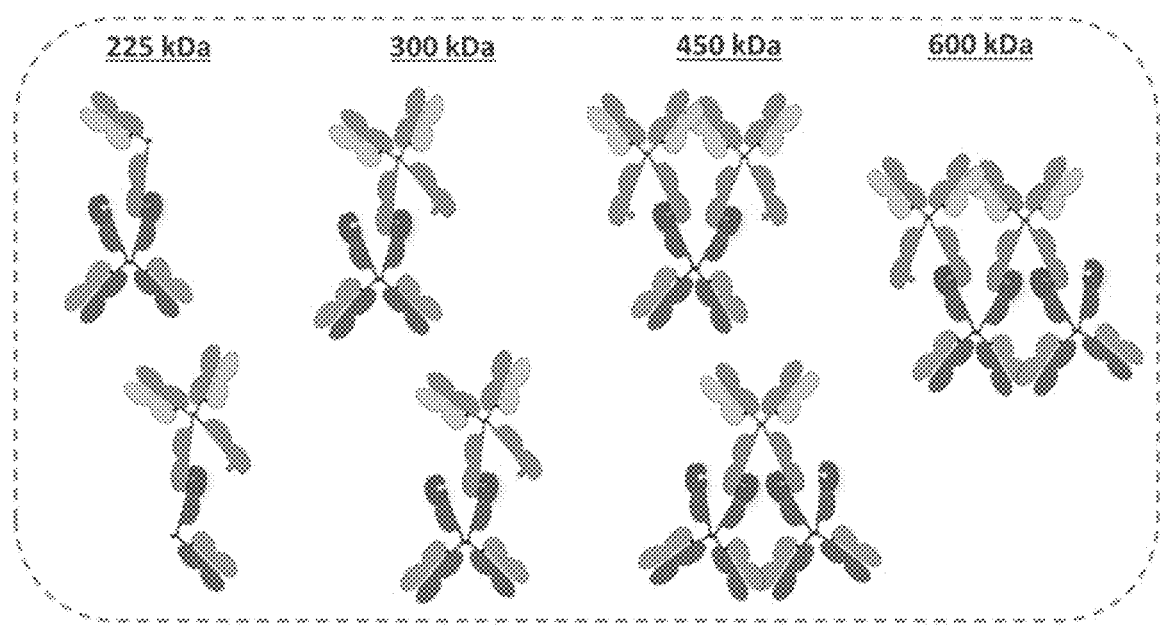
FIG. 9 depicts exemplary oligomer interaction mechanisms.

Low pH & Urea Sample Treatment: anti-CD3 and anti-CD20 homodimer species were discovered to form a high molecular weight oligomer species when present in solution together (FIG. 9). This oligomer co-migrated with the BsAb and was not detectable by this affinity assay in a quantifiable manner. Specifically, the high molecular weight oligomer was indirectly detected through the disappearance of aCD3 HD as aCD20 HD is spiked into the sample. Because the high molecular weight oligomer and BsAb comigrate, the high molecular weight oligomer species were not quantifiable in the presence of BsAb. To measure all homodimer species in solution, these oligomers need to be dissociated prior to separation. This was accomplished by preparing samples in a low pH buffer with 2M urea. These conditions were shown to dissociate the oligomer but mild enough to maintain peptide-antibody complex formation and without denaturing the BsAb structure.

Figure 7:
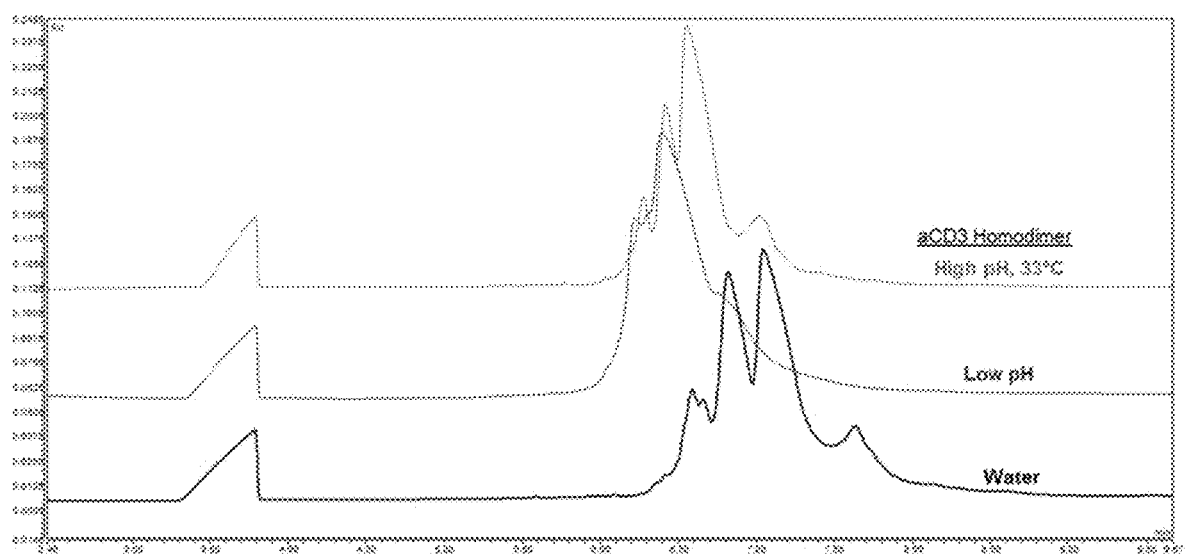
FIG. 7 depicts pH dependent conformational isomers of the anti-CD3 homodimer. Low pH sample treatment drives toward single confirmation and improves signal to noise, which is also achieved, as outlined herein, by high pH treatment.

Additionally, charged variants of the anti-CD3 HD were shown to be pH dependent. The charge of the BsAb (and associated charge variants) can have a different overall charge state and charge distribution as a function of pH. The overall charge state (e.g., total number of charges) and charge location (e.g., charge patch, buried, solvent exposed) can be different between high & low pH conditions. By preparing samples in a pH 3.5 buffer, species are driven towards a single, low-pH conformation. This improves the signal to noise, thus lowering the limit of quantitation of the assay (FIG. 7).

Figure 8:
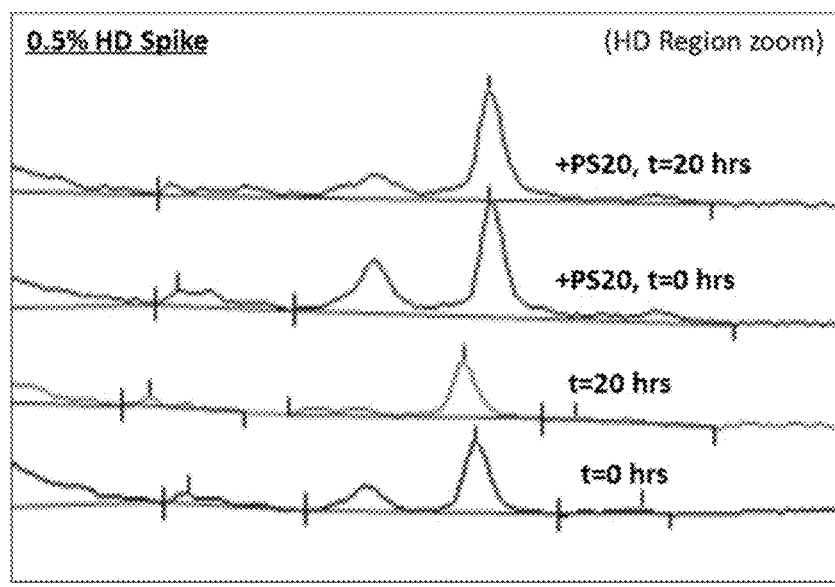
FIG. 8 depicts the improved anti-CD3 homodimer recovery over time by 0.1% PS20 in the sample.

High pH and 0.1% PS20 in Sample Matrix to Improve aCD3 HD Recovery: The anti-CD3 HD was shown to adsorb to the vial over time, resulting in lower recoveries of the anti-CD3 homodimer peak area. To control adsorption and improve recovery of anti-CD3-HD, 0.1% Polysorbate 20 (PS20) was added to the sample matrix. (FIG. 8).

Figure 10A:
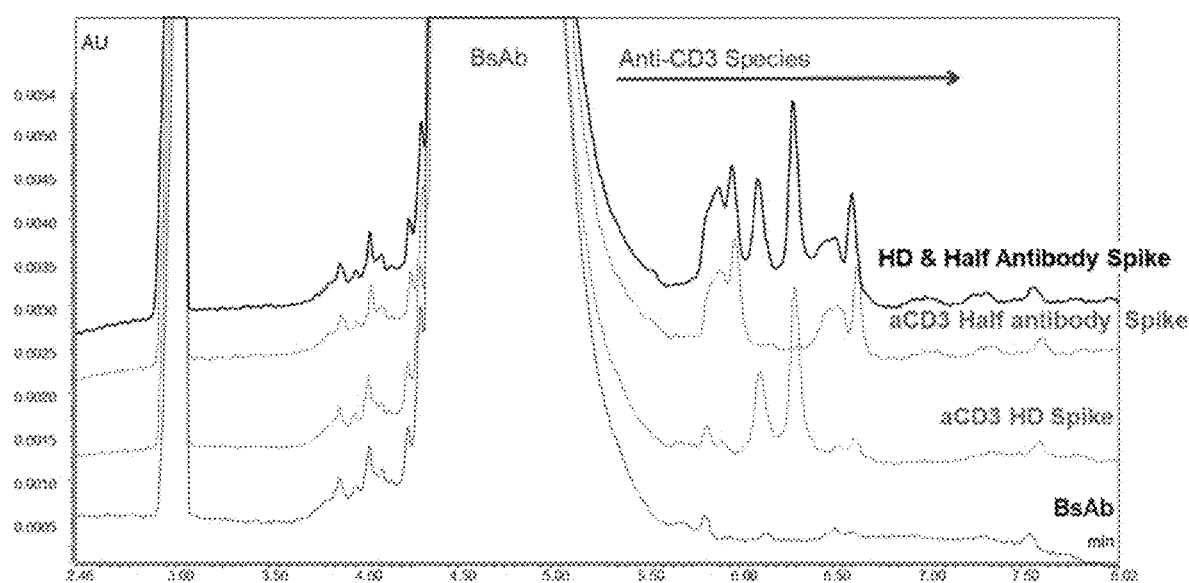
FIG. 10A-10B depicts indirect peak identification in the anti-CD3 Region via Spiked Impurities. 10A depicts results after initial mixture with HEPES buffer, while 10B depicts results after complete conversion to high pH conformation.
Figure 10B:
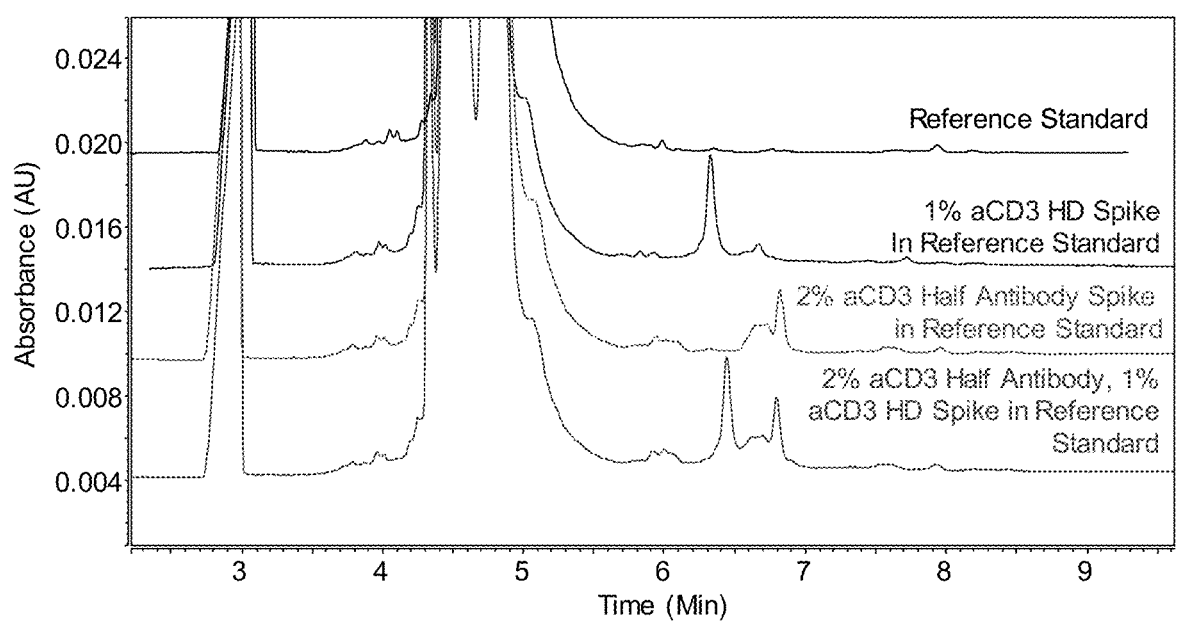

Indirect peak identification in the anti-CD3 region via spiked impurities (FIG. 10A-10B). With a 10 mM HEPES sample buffer at pH 7.5 and 0.1% PS20, improved resolution was observed between BsAb, aB half mAb and homodimer (FIG. 10A), including after allowing time for complete conversion to a high pH conformation (FIG. 10B).

Figure 11:
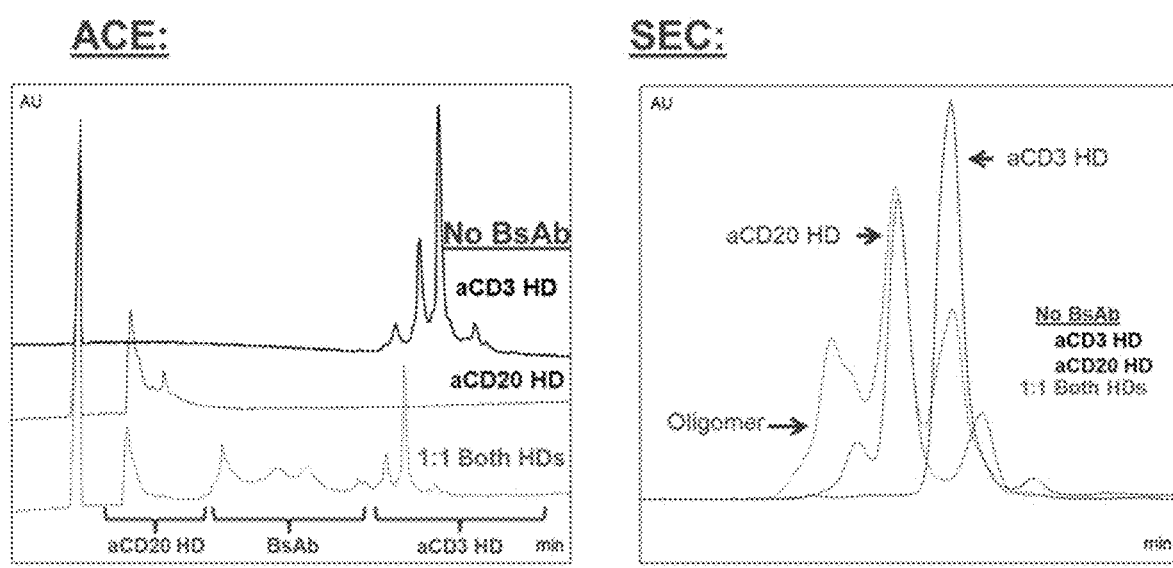
FIG. 11 depicts exemplary oligomer formation by interaction of two homodimers.
Figure 12:
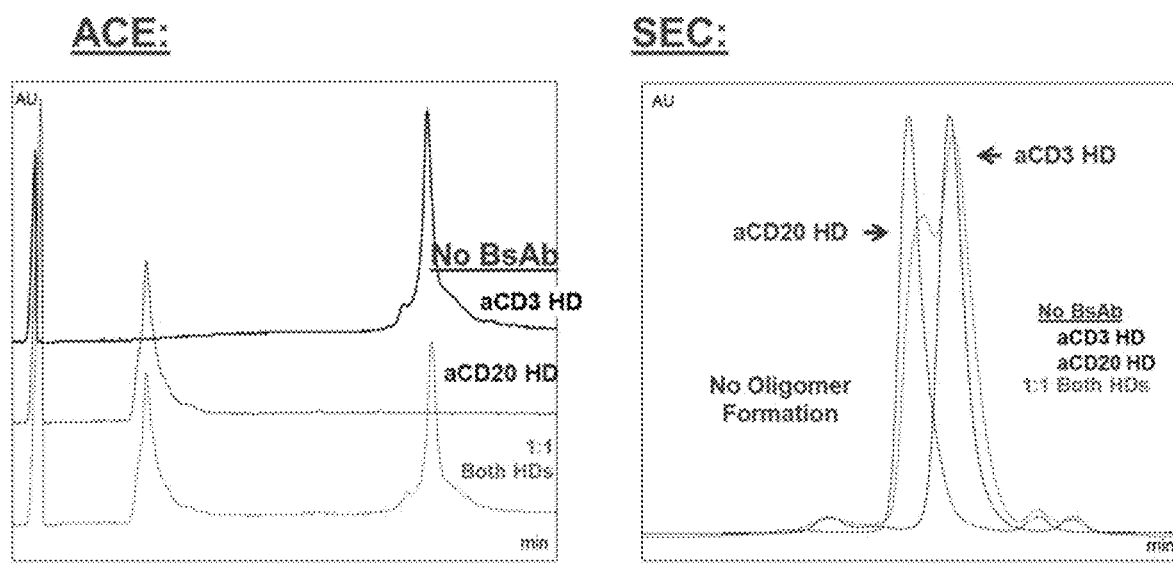
FIG. 12 depicts exemplary oligomer dissociation by low pH and urea. The sample buffer has pH 3.5 and includes urea. Urea, and low pH prevent the interaction of anti-CD3 and anti CD20 HDs (confirmed by SEC).
Figure 13:
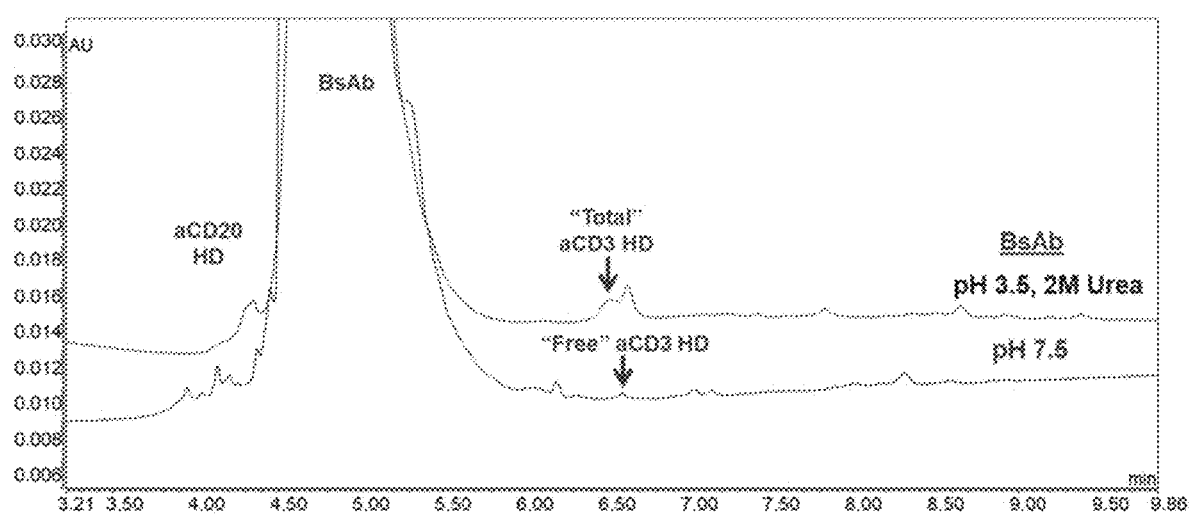
FIG. 13 depicts exemplary affinity capillary electrophoresis analysis which reveals oligomer in BsAb Reference Standard.

Oligomer formation by interaction of two homodimers was observed in ACE and size exclusion chromatography (SEC). For example, ACE showed that anti-CD3 and anti-CD20 HDs can interact and form new peaks that co-migrate with the BsAb (FIG. 11). The near peaks, "HD Complex" or "Oligomer," co-migrate with the BsAb in ACE but migrate in as high molecular weight forms by SEC. So by SEC they do not co-migrate with BsAb, they migrate before the BsAb along with other high molecular weight forms or aggregates. By SEC, however, the HD complexes are not distinguishable from other BsAb related aggregates. Such interaction was prevented by low pH and Urea. For example, the interaction of anti-CD3 and anti CD20 HDs was prevented and dissociated by low pH (e.g., pH 3.5) and urea (FIG. 12). Low pH treatment reveals a homodimer that was previously oligomerized and undetectable by other methods (FIG. 13).

Figure 14:
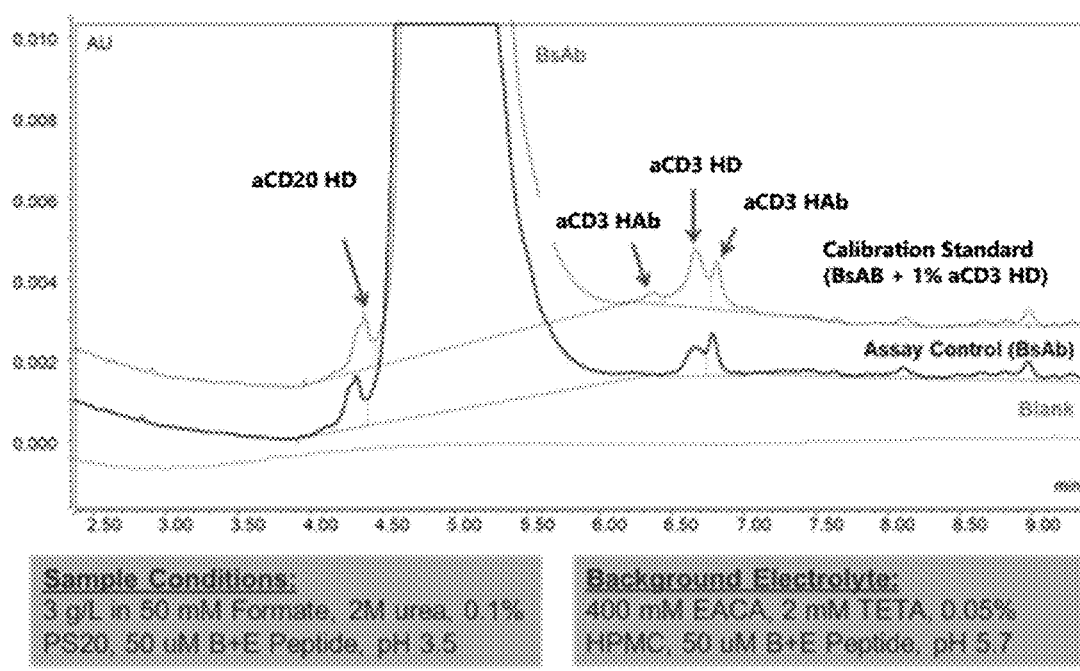
FIG. 14 depicts an exemplary low pH affinity capillary electrophoresis method.
Figure 15:
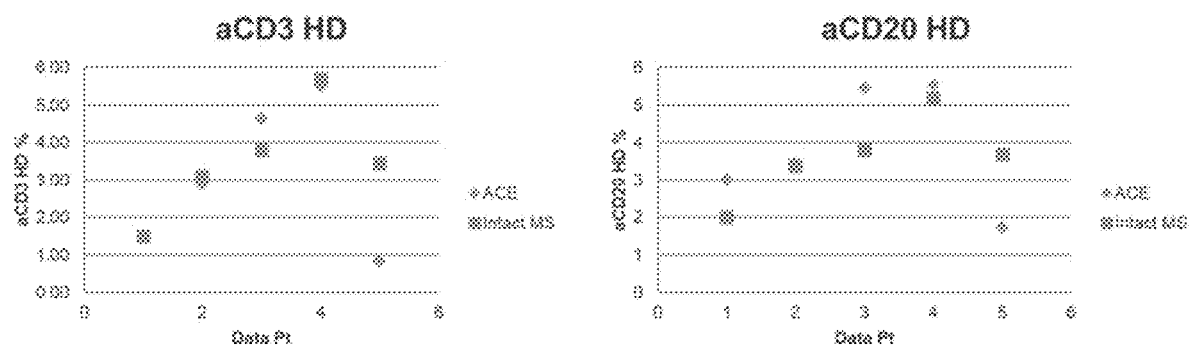
FIG. 15 depicts exemplary performance of affinity capillary electrophoresis analysis compared to the intact mass spectrometry method.

Furthermore, various modifications can be performed to improve performance of the affinity capillary electrophoresis. For example, as shown in FIG. 14, concentration of the background buffer can increase with/without sample modifications (e.g., pH adjustment, ps20 treatment, addition of ligands, urea treatment, and etc.) FIG. 14 depicts an exemplary low pH affinity capillary electrophoresis method. The disclosed systems and methods provided improved performance of ACE (FIG. 15).

What is claimed is:

1. A system for separating multi-subunit proteins in a sample comprising:
    a) a ligand modified with glutamic or aspartic acid to a non-binding region of the ligand,
    b) a background electrolyte buffer,
    c) the sample comprising multi-subunit proteins,
    d) a capillary,
    e) an anode at or near one end of the capillary, and
    f) a cathode at or near the other end of the capillary,
   wherein the sample is mixed with the ligand to form at least one ligand-protein complex comprising the ligand bound to a multi-subunit protein and loaded into the capillary at the anode end of the capillary, and
   wherein the capillary is filled with the background electrolyte buffer mixed with the ligand.

2. The system of claim 1, further comprising a detector located near the cathode end of the capillary, wherein the detector detects 210 nm to 220 nm light absorbance or laser induced fluorescence.

3. The system of claim 1, wherein the sample comprises at least one multi-subunit protein homodimer, at least one multi-subunit protein heterodimer, or a combination thereof.

4. The system of claim 3, wherein a first ligand-protein complex is formed when the ligand binds to a first subunit of the at least one heterodimer and does not bind to a second subunit of the at least one heterodimer.

5. The system of claim 3, wherein a second ligand-protein complex is formed when the ligand binds to the at least two identical first or second subunits of the homodimer.

6. The system of claim 1, wherein the at least one ligand-protein complex is configured to have an altered charge, a mass, a hydrodynamic size, an electrophoretic mobility, or a combination of thereof when the ligand binds to one or more subunits of the multi-subunit protein.

7. The system of claim 6, wherein a second ligand-protein complex has a lower electrophoretic mobility than a first ligand-protein complex.

8. The system of claim 1, wherein the ligand is a peptide or a peptide fragment.

9. The system of claim 1, wherein the ligand is selected from the group consisting of a human CD3 peptide, a mouse CD3 peptide, a rat CD3 peptide, a rabbit CD3 peptide, and a cynomolgus monkey CD3 peptide.

10. The system of claim 1, wherein the sample is further mixed with the ligand in: (A) a low pH urea buffer; or (B) a high pH HEPES buffer in combination with 0.1% Polysorbate 20.

11. The system of claim 1, wherein the background electrolyte buffer comprises Amino-n-Caproic Acid (EACA), a Triethylene tetramine (TETA), and Hydroxypropylmethyl-cellulose (HPMC).

12. A method for isolating a multi-subunit target protein in a sample mixture comprising a plurality of multi-subunit proteins comprising the steps of:
    (a) creating a mixture of the sample comprising a target multi-subunit target protein and a ligand modified with glutamic or aspartic acid to a non-binding region of the ligand to form at least one ligand-protein complex, (b) applying the mixture to a capillary, wherein the capillary is filled with a background electrolyte buffer mixed with the ligand, (c) applying a voltage across the capillary, (d) allowing the multi-subunit proteins and the at least one ligand-protein complex to move through the capillary, wherein the ligand-protein complex is configured to have an altered charge, a mass, a hydrodynamic size, an electrophoretic mobility, or a combination thereof when the ligand binds to one or more subunits of the multi-subunit target protein, and (e) isolating the target protein, which is separated from non-target proteins.

13. The method of claim 12, wherein the capillary comprises a cathode end, an anode end, and a detector.

14. The method of claim 13, wherein the detector is near the cathode end of the capillary and detects 210 nm to 220 nm light absorbance or laser induced fluorescence.

15. The method of claim 12, wherein the voltage is 30 kilovolts.

16. The method of claim 12, wherein the sample comprises at least one homodimer, at least one heterodimer, or combination thereof, wherein the at least one heterodimer comprises a first subunit and a second subunit, and the at least one homodimer comprises at least two identical first or second subunits.

17. The method of claim 16, wherein the at least one heterodimer comprises a bispecific antibody; or the at least one homodimer comprises a monoclonal antibody.

18. The method of claim 12, wherein the ligand is a peptide or a peptide fragment.

19. The method of claim 12, wherein the ligand is selected from the group consisting of a human CD3 peptide, a mouse CD3 peptide, a rat CD3 peptide, a rabbit CD3 peptide, and a cynomolgus monkey CD3 peptide.

20. The method of claim 16, wherein a first ligand-protein complex is formed when the ligand binds to the first subunit of the at least one hetero dimer and does not bind to the second subunit of the at least one hetero dimer.

21. The method of claim 16, wherein a second ligand-protein complex is formed when the ligand binds to the at least two identical first or second subunits of the homodimer.

22. The method of claim 12, further comprising: (A) mixing a low pH urea buffer to the mixture of the sample and the ligand; or (B) mixing a high pH HEPES buffer in combination with 0.1% Polysorbate 20 to the mixture of the sample and the ligand.

23. The method of claim 12, wherein the background electrolyte buffer comprises Amino-n-Caproic Acid (EACA), a Triethylene tetramine (TETA), and Hydroxypropyl methylcellulose (HPMC).

24. The method of claim 12, further comprising quantifying the amount of the target protein in the sample.

25. An affinity capillary electrophoresis ligand comprising:

(a) a binding region, wherein said binding region binds or is bound by a protein of interest;

(b) a modification where said modification facilitates the isolation of the protein of interest and the ligand is modified with glutamic or aspartic acid to a non-binding region of the ligand.

26. The ligand of claim 25 wherein the protein of interest is a homodimer or a heterodimer.

27. The ligand of claim 25 wherein the binding region is a polypeptide.

28. The ligand of claim 25 wherein the binding region is a small molecule.

* * * * *